(12) United States Patent
Ciampini

(10) Patent No.: US 10,761,080 B2
(45) Date of Patent: Sep. 1, 2020

(54) DETECTING A MARKER IN A LIQUID

(71) Applicant: SICPA HOLDING SA, Prilly (CH)

(72) Inventor: Davide Ciampini, Pavone Canavese (IT)

(73) Assignee: SICPA HOLDING SA, Prilly (CH)

( * ) Notice: Subject to any disclaimer, the term of this patent is extended or adjusted under 35 U.S.C. 154(b) by 172 days.

(21) Appl. No.: 15/329,859

(22) PCT Filed: Mar. 17, 2015

(86) PCT No.: PCT/EP2015/055534
§ 371 (c)(1),
(2) Date: Jan. 27, 2017

(87) PCT Pub. No.: WO2016/050364
PCT Pub. Date: Apr. 7, 2016

(65) Prior Publication Data
US 2017/0269056 A1    Sep. 21, 2017

(30) Foreign Application Priority Data

Sep. 30, 2014   (EP) .................... 14187065

(51) Int. Cl.
*G01N 27/26* (2006.01)
*B01L 3/00* (2006.01)
(Continued)

(52) U.S. Cl.
CPC .... *G01N 33/2882* (2013.01); *B01L 3/502707* (2013.01); *B01L 3/502715* (2013.01);
(Continued)

(58) Field of Classification Search
CPC .... G01N 27/26; G01N 27/00; G01N 33/2882; G01N 33/2835; G01N 33/28;
(Continued)

(56) References Cited

U.S. PATENT DOCUMENTS

| 2002/0122747 | A1* | 9/2002 | Zhao | B01L 3/502707 422/400 |
| 2002/0142477 | A1* | 10/2002 | Lewis | G01N 33/0031 436/151 |
| 2004/0040841 | A1* | 3/2004 | Gonzalez-Martin | G01N 27/126 204/406 |

(Continued)

FOREIGN PATENT DOCUMENTS

WO    2007143541    12/2007

OTHER PUBLICATIONS

Eurasia office action in counterpart Eurasian Application No. 201690359/31 dated Dec. 6, 2016 (and English language translation).
(Continued)

*Primary Examiner* — Christine T Mui
(74) *Attorney, Agent, or Firm* — Muncy, Geissler, Olds & Lowe, P.C.

(57) ABSTRACT

A detection device for detecting a marker in a liquid, comprising a reaction chamber, provided with a thermosensitive sensor, wherein said reaction chamber comprises an photopolymer capable of releasing or generating a chemical species that is capable of undergoing or initiating an exothermic or endothermic chemical reaction with a marker present in the liquid.

21 Claims, 8 Drawing Sheets

(51) Int. Cl.
*G01N 33/28* (2006.01)
*G01N 25/48* (2006.01)
*C09D 163/04* (2006.01)

(52) U.S. Cl.
CPC ...... *B01L 3/502723* (2013.01); *C09D 163/04* (2013.01); *G01N 25/488* (2013.01); *G01N 25/4873* (2013.01); *B01L 2200/12* (2013.01); *B01L 2300/0627* (2013.01); *B01L 2300/16* (2013.01); *B01L 2300/161* (2013.01); *B01L 2300/18* (2013.01)

(58) Field of Classification Search
CPC .. G01N 33/26; G01N 33/24; B01L 3/502707; B01L 3/5027; B01L 3/502; B01L 3/50
USPC .......................................................... 204/406
See application file for complete search history.

(56) References Cited

U.S. PATENT DOCUMENTS

2005/0182149 A1* 8/2005 Crivello ................ B01J 19/123
522/4
2008/0056946 A1 3/2008 Ahmad

OTHER PUBLICATIONS

"Thermopile Sensors for the detection of Airborne Pollutants", Sensors, 2007 IEEE, IEEE, PI, Oct. 28, 2007 (Oct. 28, 2007), pp. 1237-1240, XP031221293, ISBN: 978-1-4244-1261-7.
International Search Report and Written Opinion issued with respect to application No. PCT/EP2015/055534.

* cited by examiner

DETECTING A MARKER IN A LIQUID

TECHNICAL FIELD

The technical field of the present invention is the thermal detection of reactive molecules in a liquid environment. Specifically, the present invention relates to a detection device for detecting a marker in a liquid. The present invention likewise relates to related systems and methods.

BACKGROUND OF THE INVENTION

Currently, enthalpy changes due to chemically reactive species are detected using bench laboratory equipment, as DSC (Differential Scanning calorimeter) or Photo-DSC analyzer. DSC equipment yield accurate information, but they can be big and expensive. Moreover, their operation may require skilled people and the performed analysis can be time-consuming.

The object of the invention is to provide a cheap and portable solution for the detection of specific markers that can be detected when dissolved in a liquid at low concentration, in particular in fuel liquids, such as refined petroleum products including gasoline, diesel, kerosene, etc. The markers preferably have a good solubility in the liquid, and are preferably difficult to be identified, extracted and separated. The proposed solutions preferably provide a fast and reliable detection of the presence of a marker in a liquid, such as liquid fuel.

SUMMARY OF THE INVENTION

The mentioned problems and objects are solved by the subject-matter of the independent claims. Further preferred embodiments are defined in the dependent claims and are also described in the following specification.

According to an embodiment of the present invention there is provided a detection device for detecting a marker in a liquid, comprising a reaction chamber, provided with a thermosensitive sensor, wherein said reaction chamber comprises an photopolymer capable of releasing or generating a chemical species that is capable of undergoing or initiating an exothermic or endothermic chemical reaction with a marker present in the liquid.

According to another embodiment of the present invention there is provided a system comprising a detection device according to a corresponding embodiment of the present invention, a fuel as said liquid; and a marker dissolved in the fuel with a concentration <150 ppm, which is preferably an epoxy compound.

According to another embodiment of the present invention there is provided a method for manufacturing a detection device according to any one of steps 1 to 10 comprising the steps of: depositing a photocurable epoxy composition layer exhibiting an excess of photoinitiator on the walls and/or on the floor of a reaction chamber and/or on a thermosensitive sensor placed in the reaction chamber; photocuring with UV radiation the photocurable epoxy composition layer exhibiting an excess of photoinitiator, so that unreacted acid molecules resulting from the decomposition of the photoinitiator maintain in the bulk and/or on the surface of the acidified photopolymer layer.

According to yet another embodiment of the present invention there is provided a method for detecting a marker in a liquid, comprising the steps of introducing the marked liquid into the reaction chamber of a detecting device according to any one of a corresponding embodiment; letting the marker react in the reaction chamber with a chemical species released or generated from the photopolymer to cause a temperature increase or decrease at the position of the thermosensitive sensor by an exothermic or endothermic reaction of the marker and the chemical species released or generated from the photopolymer; and measuring the voltage or current output generated by the thermosensitive sensor placed in the reaction chamber.

BRIEF DESCRIPTION OF THE DRAWINGS

Embodiments of the present invention, which are presented for better understanding the inventive concepts and which are not to be seen as limiting the invention, will now be described with reference to the figures in which.

DETAILED DESCRIPTION

Figure 1:
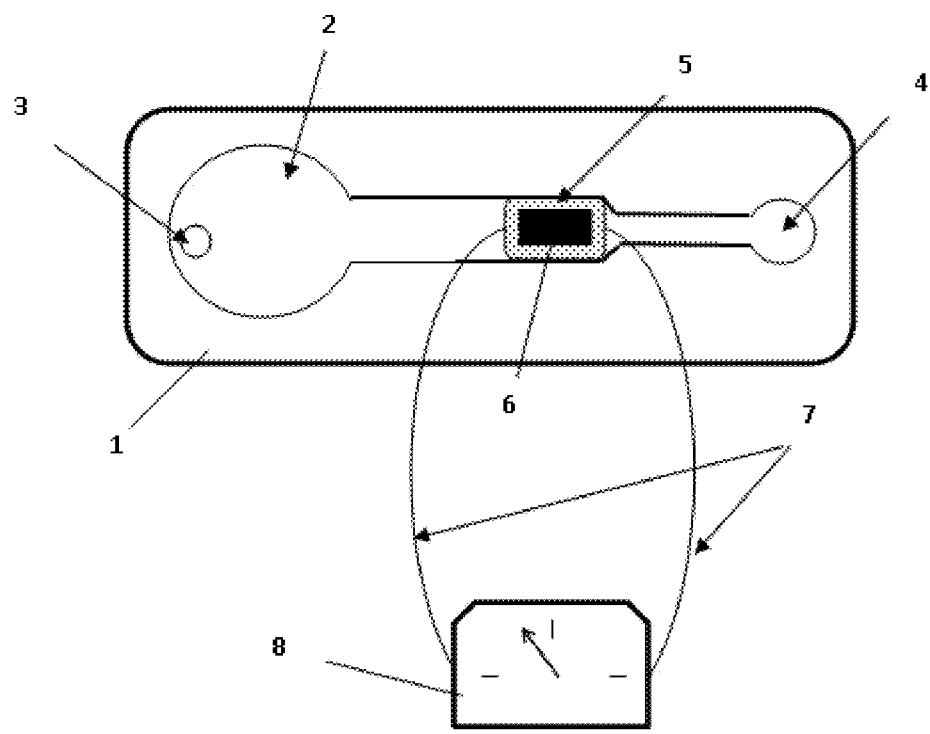
FIG. 1 shows a schematic view of a single sensor enthalpy detecting device according to an embodiment of the present invention.

According to an embodiment of the present invention, a detection device is provided that is able to identify a highly diluted marker in a liquid by measuring the reaction enthalpy of the reaction between said marker and a component inside the device. According to a further embodiment of the present invention, a device can be achieved that detects low concentrations of different types of markers diluted in a fuel (at total concentration of preferably 100 ppm for all markers). Such devices can contain a polymer able to release a chemical species (preferably an acid) that reacts with the marker dissolved in the liquid, developing a reaction heat that can be in turn detected by a pyroelectric thermal sensor provided in the device, preferably close to the polymeric active surface. The sensor signal can be preferably a function of the kinetic reaction mechanism.

In order to have a lab-on-chip of small size able to detect one or more markers solubilized in the liquid fuel at a total concentration equal to or lower than 100 ppm, a device according to an embodiment of the invention can contain a photopolymeric material able to generate or release acidic species and a pyroelectric sensor able to detect temperature variations of a liquid close to the photopolymeric material. The device of a corresponding embodiment comprises three communicating areas: an injection chamber where the marked fuel is introduced; a reaction chamber, where the thermosensitive sensor is placed, that is connected to the injection chamber and that contains the photopolymeric layer capable of releasing the chemical species that reacts with the marker; and a third chamber, connected to the reaction chamber, used for venting the device.

The marker dissolved in the fuel reacts with a chemical species, preferably an acid, released or generated by the photopolymer; and the reaction generates or absorbs heat (exothermic or endothermic reaction) with a distinctive kinetic profile. The reaction heat produces a temperature variation (i.e. a temperature increase or decrease, depending on the reaction being exothermic or endothermic) on the sensor located in the device; and the sensor, as a consequence of the temperature variation, generates a voltage or current signal. The shape of the curve resulting from the voltage/current signal vs. time highly depends on the type of the one or more markers and their respective concentration, as well as on the chemical characteristics of the photopolymeric layer contained in the reaction chamber, in particular the kind and amount of the chemical species that is released or generated and its reaction kinetics with the one or more marker.

According to a further embodiment, the device is configured to detect or react to the presence of one or more reactive markers dissolved in a liquid. In principle, any compound that is capable of reacting with the chemical species (preferably an acid) that is released by the photopolymer can be used as a marker, as any such reaction will either be endothermic or exothermic and will give rise to a certain shape of the curve measured as signal by the sensor.

The marker of the present invention is preferably one or more compounds selected from the following:

inorganic and organic bases, of which organic bases are preferable, with aliphatic or aromatic amines being more preferable, and which further preferably have one or more basic nitrogen atoms;

compounds capable of undergoing an addition reaction upon contact with the chemical species released by the photopolymer, preferably ethylenically unsaturated compounds, more preferably those having a terminal ethylenically unsaturated group, including compounds having a vinyl, allylic, or vinylether group.

esters, preferably carboxylic acid esters, which are preferably able to undergo saponification upon reaction with the chemical species released by the photopolymer;

silanes of formula $SiR_1R_2R_3R_4$, wherein at least one of $R_1$, $R_2$, $R_3$, and R represents a hydrogen atom and the remaining represent an organic group, preferably an alkoxy group having 1 to 6 carbon atoms, compounds having an epoxy group which are preferably able of performing a ring-opening reaction upon contact with the chemical species released by the photopolymer, preferably compounds having more than one epoxy group, methacrylates and acrylates (in the following commonly referred to as (meth)acrylates), which are preferably $C_{1-6}$ alkyl esters of acrylic acid and methacrylic acid; and alcohols having one or more hydroxyl groups, preferably aliphatic alcohols or aromatic alcohols, such as ethanol, propanol, butanol, hexanol or phenol.

In this group, amines and epoxy compounds are preferred.

Each molecule belonging to these chemical classes will exhibit a distinctive kinetic reaction curve. This will allow the device to identify its presence and concentration in a liquid, e.g. by comparing the obtained signal with a predetermined expected (stored) signal or curve.

In the method for detecting a marker, the marker may serve as authenticating means for authenticating the quality and/or origin of the liquid. For this purpose, the marker is typically present in a concentration of 1,000 ppm or less, preferably 500 ppm or less, and more preferably 100 ppm or less, in the liquid to be tested. Herein and throughout the description, values referred to in ppm or % are by weight.

The liquid contains one or more markers. Herein and throughout the description, the phrase "one or more" is used to denote that one or more of the respective element is present, such as one, two, three, four, five, six, or seven. Preferably, "one or more" means one, two or three.

In a preferred embodiment the device is especially adapted to work with epoxies, vinylethers and amines. For these three classes, there are different types of reactions, including a ring opening cationic addition mechanism (which may be a polyaddition); a cationic addition mechanism (which may be a polyaddition); and an acid-base reaction.

Generally, a device according to embodiments of the invention can be made in a two-part configuration, including a top part and a bottom part that are assembled together within a precise alignment using different techniques like heat bonding, adhesive bonding, solvent bonding, laser welding etc.

FIG. 1 shows a schematic view of a single sensor enthalpy detecting device according to an embodiment of the present invention.

The shown device comprises a substrate 1 made of organic or inorganic material that is preferably resistant to the target liquid, such as fuel. The material is preferably suitable for mechanic machining, so that it can be well machined by mechanical manufacturing techniques (drilling, milling, etc . . . ) or photolithographic patterning, in order to obtain the hydraulic circuit and the inlet/outlet holes.

The device is provided with an injection chamber 2 having an inlet 3 for introducing the liquid or fuel. The injection chamber is in communication with the reaction chamber 5 where the pyroelectric sensor 6 is arranged.

A suitable pyroelectric sensor of small size can be, for example, provided as a pyroelectric device that comprises a plurality of layers of a polar dielectric material exhibiting pyroelectric properties. The device may further comprise a plurality of conductive electrodes, wherein each conductive electrode is substantially in contact with at least a portion of one surface of a respective at least one of said plurality of layers of polar dielectric material. Said electrodes are then electrically connected in a parallel configuration as to form a series of capacitors comprised of said plurality of layers of polar dielectric material and plurality of conductive electrodes. By means of such a configuration, a pyroelectric sensor can be obtained that provides a sufficiently small form factor as well a sufficient sensitivity in terms of output signal resolution vs. heat exchange in the active region and time.

Next, the photopolymer capable of releasing the chemical species that reacts with the marker is described.

In the present invention, the term "photopolymer" is used to denote a polymer that is produced by reaction of a polymerizable composition including monomers by initiation of the polymerization reaction by means of a photopolymerization initiator. That is, the polymerizable composition is irradiated with electromagnetic radiation (typically UV light with a wavelength in the range from 200 to 380 nm, or with light of a wavelength of e.g. up to 450 nm) to decompose a photopolymerization initiator. Thereby, the photopolymerization initiator is decomposed, causing the formation of radicals or other species (such as cations) capable of initiating the polymerization reaction of the polymerizable components in the polymerizable composition.

Using a suitable process, the photopolymeric material is deposited on the walls and the floor of the reaction chamber and/or on the sensor 6 itself. The reticulation is carried out by means of UV radiation using a traditional UV mercury lamp or a LED irradiation system. The polymerization reaction is initiated by means of UV radiation using a conventional UV mercury lamp or a LED irradiation system.

The photopolymer is typically an epoxy based material that can provide high chemical resistance to the liquid (e.g. the fuel) after the photocuring. It is crucial that the formed photopolymer is able to generate or release a chemical species that is capable of reacting with the marker present in the liquid fuel.

This species may be included in the photopolymer at the time of contact with the liquid, and is then released into the liquid to react therewith, such as in the case of an acid resulting from an excess of (cationic) photoinitiator used and decomposed at the time of forming the photopolymer. Yet, the chemical species may also be generated by the photopolymer as reaction to an external stimulus. For instance, it is envisaged to use a photopolymer that is able to generate acids under irradiation in the UV (200-380 nm) or visible spectrum. Also, it is envisages that a part of the photoinitiator contained in the formulation remains unreacted until contact with the liquid in the device. During the contact, an external stimulus may be used to generate the chemical species (e.g. the acid), for instance by UV exposure.

One way how this can be achieved is e.g. by employing an excess of photoinitiator, which is able to generate the chemical species that reacts with the marker molecule. This chemical species may for instance be acid molecules that are reactive with the marker, leading to e.g. polymerization or ring-opening reaction of epoxy functionalities.

The exceeding unreacted chemical species, e.g. the acid, remains absorbed inside the bulk of the photopolymer and adsorbed on the surface of the photopolymer. A suitable outlet 4 allows the correct liquid flow, venting the hydraulic circuit.

In the present invention, the photopolymer is capable of generating or releasing a chemical species that reacts with the marker in the liquid in an exothermic or endothermic reaction.

The chemical species released or generated by the photopolymer can be any compound capable of reacting with the marker in an endothermic or exothermic reaction, but is preferably an acid. Herein, the term "acid" is not limited to Bronsted-acids, but also includes Lewis-acids. Preferably, the acid is a Bronsted acid, and further preferably is a Bronsted having a pKa of 5 or less, more preferably 1 or less, and even further preferably 0 or less. It above all preferable that the acid is a superacid, i.e. is an acid with an acidity greater than that of 100% pure sulfuric acid, which has a Hammett acidity function (HO) of −12. Examples of such acids include hexafluoro antimonic acid or hexafluoro phosphoric acid.

The top device part comprises a printed circuit board (PCB) to which the pyroelectric sensor 6 is bonded and two conductive tracks 7 led out the signal from the sensor to an external circuit, such as an instrument 8 (data acquisition hardware or an oscilloscope, for example) in order to collect the data. When the liquid or fuel, containing a reactive marker, is injected into the device, it contacts the photopolymer close to the pyroelectric sensor. The photopolymer released the chemical species, e.g. an acid, and the reaction takes place on the photopolymer surface. The sensor measures the reaction heat and the signal is read out by the electrical tracks of the PCB. The recording instrument 8 generates a plot of voltage (or current) as a function of time. The plot shape will be dependent on the kinetic of the reaction and so it will depend on the molecule type and its concentration inside the fuel. In general, the signal indicates the temperature change over time.

A prototypal device implementing an embodiment of the present invention has been prepared to comprise a reaction chamber coated with a photopolymer capable of releasing an acid and a pyroelectric sensor nearby. An oscilloscope has been interfaced to the sensor which detects the temperature variations inside the reaction chamber, in order to collect a plot with the voltage vs. time. In this prototypal device two different liquids have been injected in sequence: (1) fuel (diesel) without additive (cf. FIG. 2); and (2) fuel (diesel) containing a reactive marker (approx. 100 ppm of 1,2-epoxy-2-methylpropane) (cf FIG. 3).

In each experiment the injected liquid and the sensor initially were not at the same temperature. According to a further embodiment, a configuration can be provided for bringing the liquid and the sensor into thermal equilibrium, by means of, for example, a suitable thermostatic ancillary equipment, in order to have no cooling effect during the first contact of the liquid to the sensor. This may be particularly advantageous for a more secure identification of the marker, as the measured signal reflects the reaction kinetics of the reaction. The shape of the obtained signal curve may then be different for different temperatures, as the reaction kinetics can differ at different temperatures.

Figure 2:
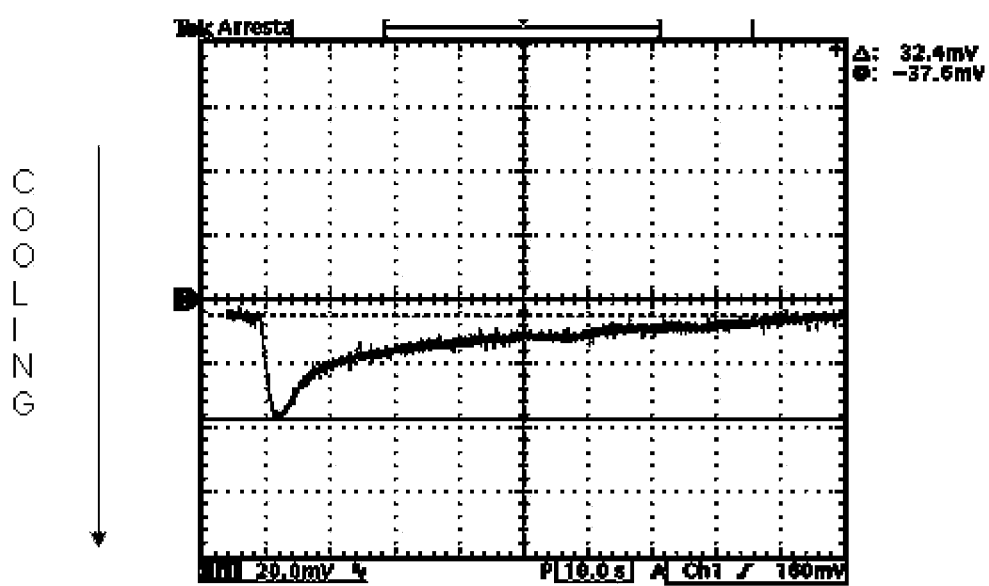
FIG. 2 shows an exemplary characteristic curve of a cold unmarked fuel.

FIG. 2 shows an exemplary characteristic curve of a cold (near to 20° C.) unmarked fuel. Specifically, the results are shown of the first test performed with simple fuel, without any marker: the liquid was at a lower temperature with respect to the sensor, so the oscilloscope recorded a negative voltage variation, due to the cooling down of the pyroelectric device. There was also no reactive additive other than a marker in the fuel, therefore there appeared no evidence of a heating effect due to exothermic reactions within the device chamber. As a consequence, the temperature difference between the liquid and sensor plays the major role in the output voltage signal.

Figure 3:
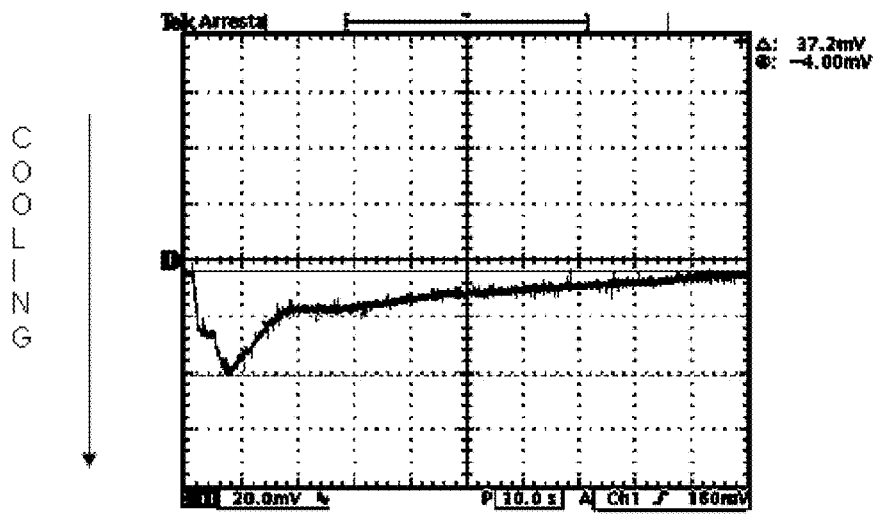
FIG. 3 shows an exemplary characteristic curve of a cold marked fuel with approx. 100 ppm concentration.

FIG. 3 shows an exemplary characteristic curve of a cold marked fuel. In this second test, the fuel contained approx. 100 ppm of a reactive marker (1,2-epoxy-2-methylpropane) was injected into the reaction chamber. The output signal is shown in FIG. 3, where, during the first few seconds, one observes an opposing effect that contrasts the sensor cooling observed and described in conjunction with FIG. 2: after the first descending part of the curve, due to the sudden contact between liquid and sensor, there is a nearly flat portion, indicating that an exothermic effect was contrasting the cooling. This exothermic effect is a heating effect caused by the expected exothermic reaction of the reactive marker with the acid species released by the photopolymer, close to the sensor.

As expected, the reaction can be quite fast and as a consequence of the low concentration it can be advisable to "zoom-in" on the thermogram, focusing onto the first seconds in order to have a more precise analysis. As previously mentioned, a possible further improvement could include a temperature matching of the fuel and the sensor before letting the reaction take place. This would avoid the physical cooling effect and the pure reaction signal would be obtained.

Figure 4:
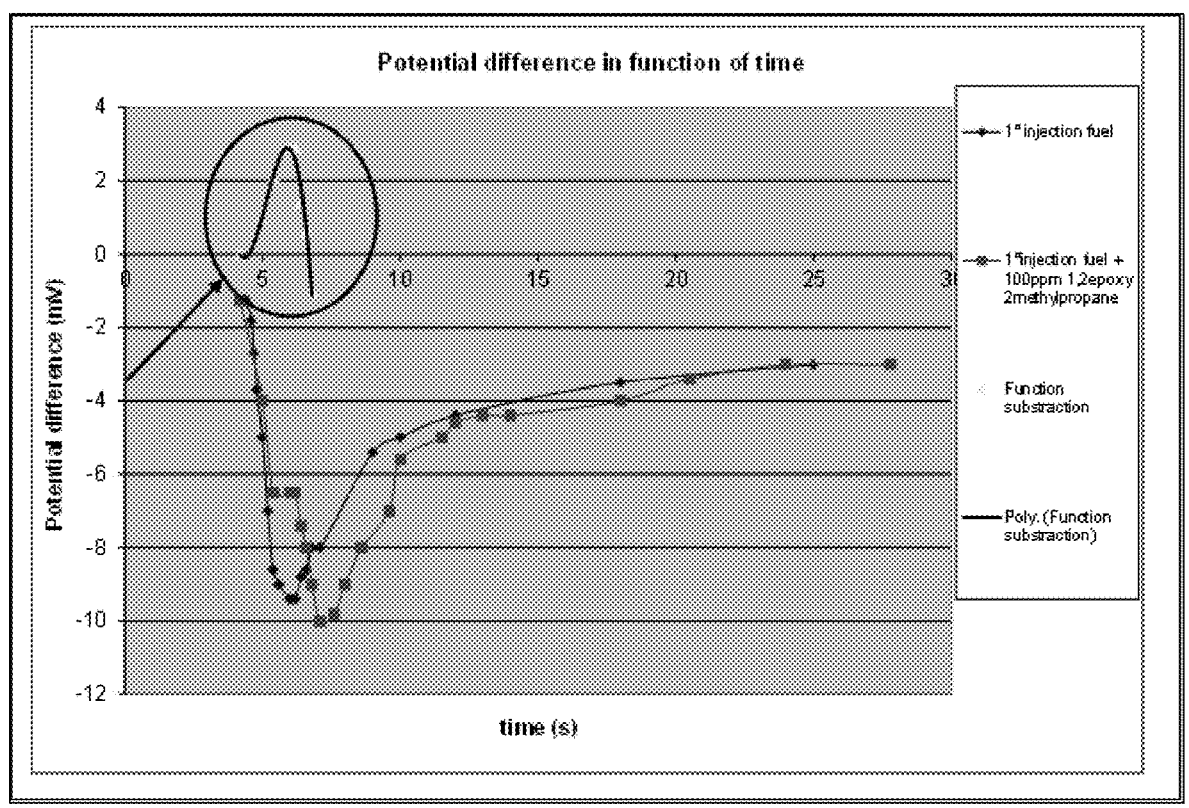
FIG. 4 shows an example of a calculated difference between the curves in FIGS. 2 and 3.

FIG. 4 shows an example of a calculated difference between the curves in FIGS. 2 and 3. In preliminary tests, the signal has been cleaned from the unwanted cooling effect subtracting numerically the first experimental curve (cf. FIG. 2) from the second one (cf. FIG. 3). The result of this difference operation is depicted in FIG. 4 that demonstrates the net signal depending on the chemical reaction. In this graphic the subtraction of the two plots is highlighted: the shape of this function and in particular its integral and the peak voltage value reached is dependent on the enthalpy and on the reaction kinetic of the additive with the acid species generated from the photopolymer formulation. It can be of advantage to get a high reproducibility of both reaction chambers and sensors with respect to the processes and materials adopted in the device manufacturing (shape, uniformity of the photopolymeric coating, width, sensor sensitivity, etc.).

Figure 5:
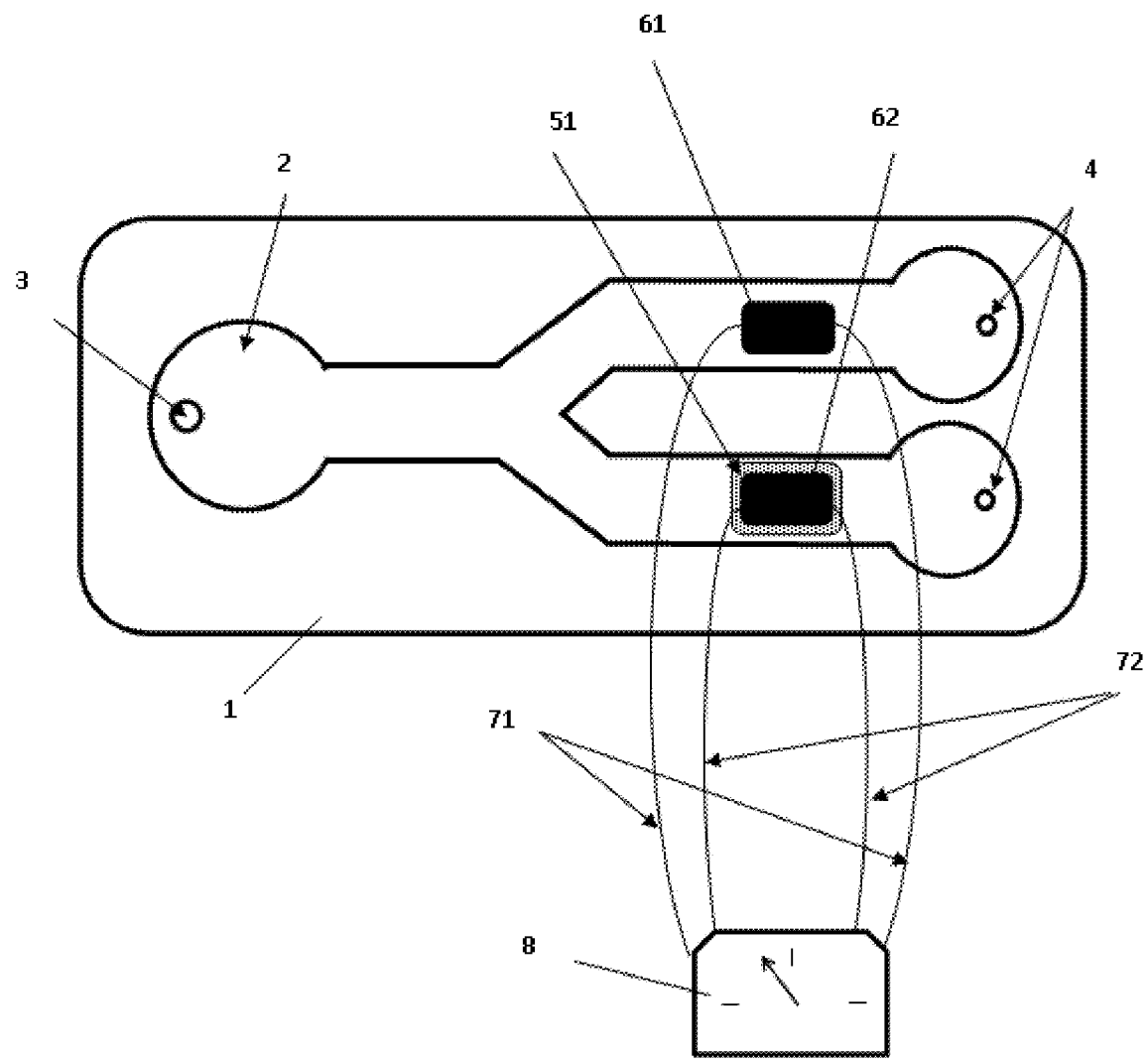
FIG. 5 shows a schematic view of a dual sensor differential enthalpy detecting device according to an embodiment of the present invention.

FIG. 5 shows a schematic view of a dual sensor differential enthalpy detecting device according to an embodiment of the present invention. According to this embodiment, a differential approach is adopted to simplify the detection equipment. In this case, after the injection chamber 2 the fuel splits up in two flowpaths, reaching at the same time, but independently, two pyroelectric sensors 61 and 62 arranged in two separated/different chambers. The outlets 4 allow the venting of the hydraulic circuit. Only one of these two chambers will contain the photopolymer 51 so that only in this chamber the reaction will take place. Both the sensors will record the effect due to the different temperature of the liquid with respect to the sensor, but only one will detect also the reaction heating, because of the presence of the chemical species released or generated by the photopolymer inside its own chamber. Choosing the suitable poling direction for each sensor and connecting them opportunely through the wires 71 and 72, a differential signal can be directly obtained and recorded or displayed in the measuring equipment 8, without the need of numerical operations. This embodiment could avoid the need of the preliminary temperature matching of fuel and sensor.

In the fuel marker detecting devices according to embodiments of the present invention, the photopolymer 5 can be arranged as close as possible to the pyroelectric sensor 6, so that the heat generated through the reaction at the polymer surface can cause an appreciable and well-pronounced effect in the sensor, before spreading throughout the whole liquid. Therefore, the reaction chamber size can be designed to house the sensor, allowing the liquid to flow without leaving too much room between the chamber walls and the sensor surface.

A possible alternative solution is to coat the surface of the sensor itself with the photopolymer, instead of or in addition to coating the reaction chamber walls: the close proximity between the sensor and the reactive surface can allow for a very effective response of the sensor to the heat generated by the reaction. Such a situation is also depicted in FIG. 5, where the sensor 61 is uncoated, whilst the sensor 62 has on its own surface the photopolymer coating 51, able to react with the fuel marker. Of course, the previous solution, where the coating is on the internal chamber walls, could be conveniently pursued also in a differential embodiment.

Figure 6:
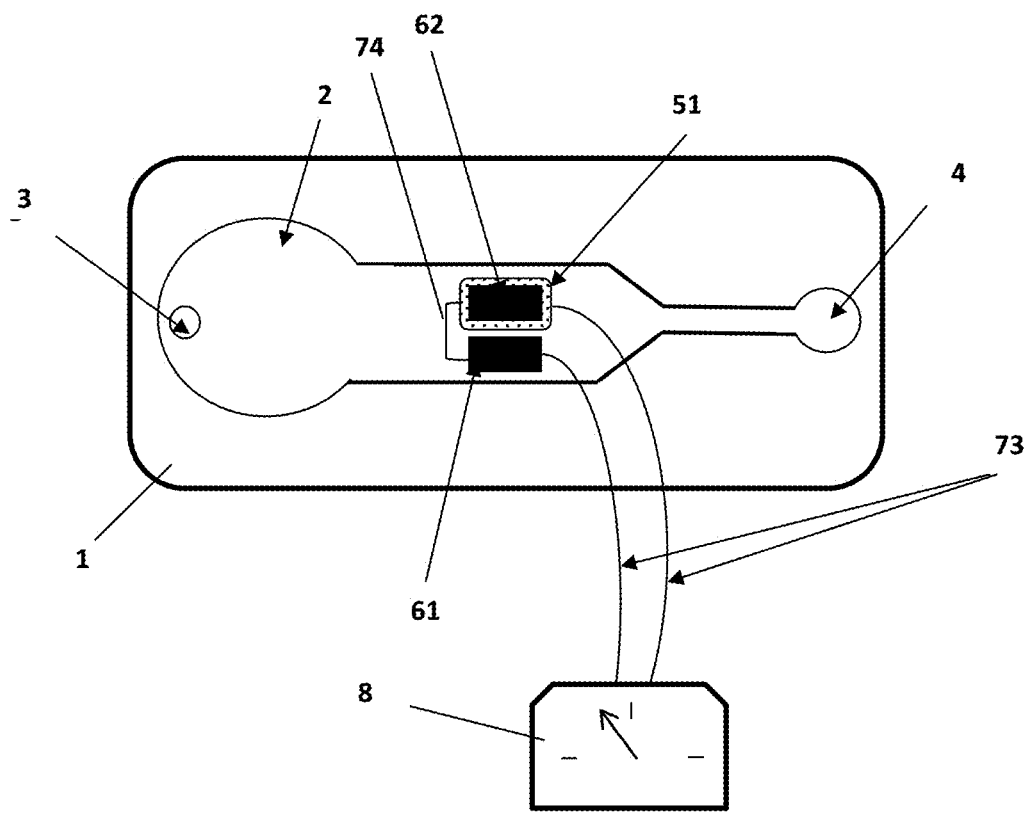
FIG. 6 shows a schematic view of a dual sensor differential enthalpy mono-channel detecting device according to an embodiment of the present invention.

FIG. 6 shows a schematic view of a dual sensor differential enthalpy mono-channel detecting device according to an embodiment of the present invention. There, the differential approach is accomplished in a device with a single reaction chamber; this solution can provide the advantage to have a simplified hydraulic circuit. In this embodiment the uncoated sensor 61 and the coated one 62 are connected at one end with the contact lead 74, whilst the other ends, through the wires 73, provide the differential electrical signal for the measuring equipment 8.

Figure 7:
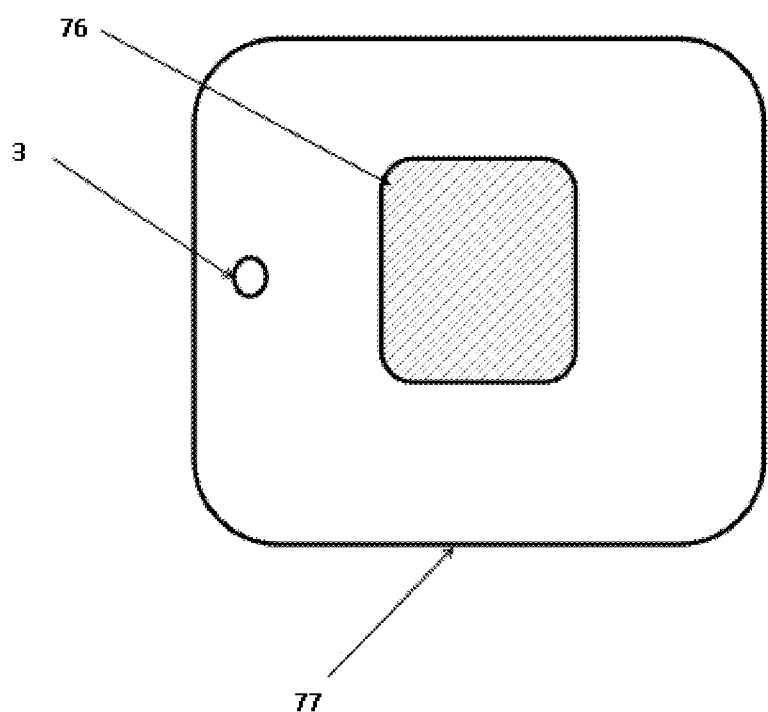
FIGS. 7, 8, and 9 show schematic views of a dual sensor differential enthalpy vapor detecting device (bottom layer) according to an embodiment of the present invention.
Figure 8:
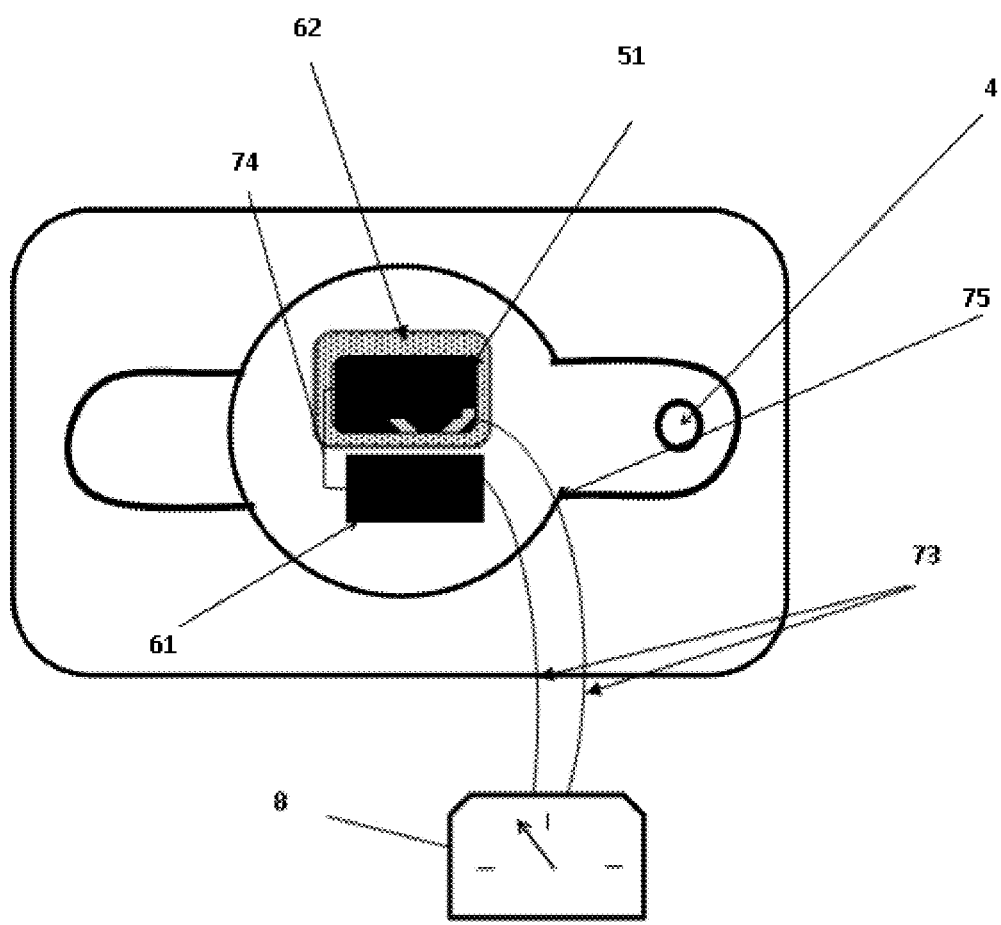
Figure 9:
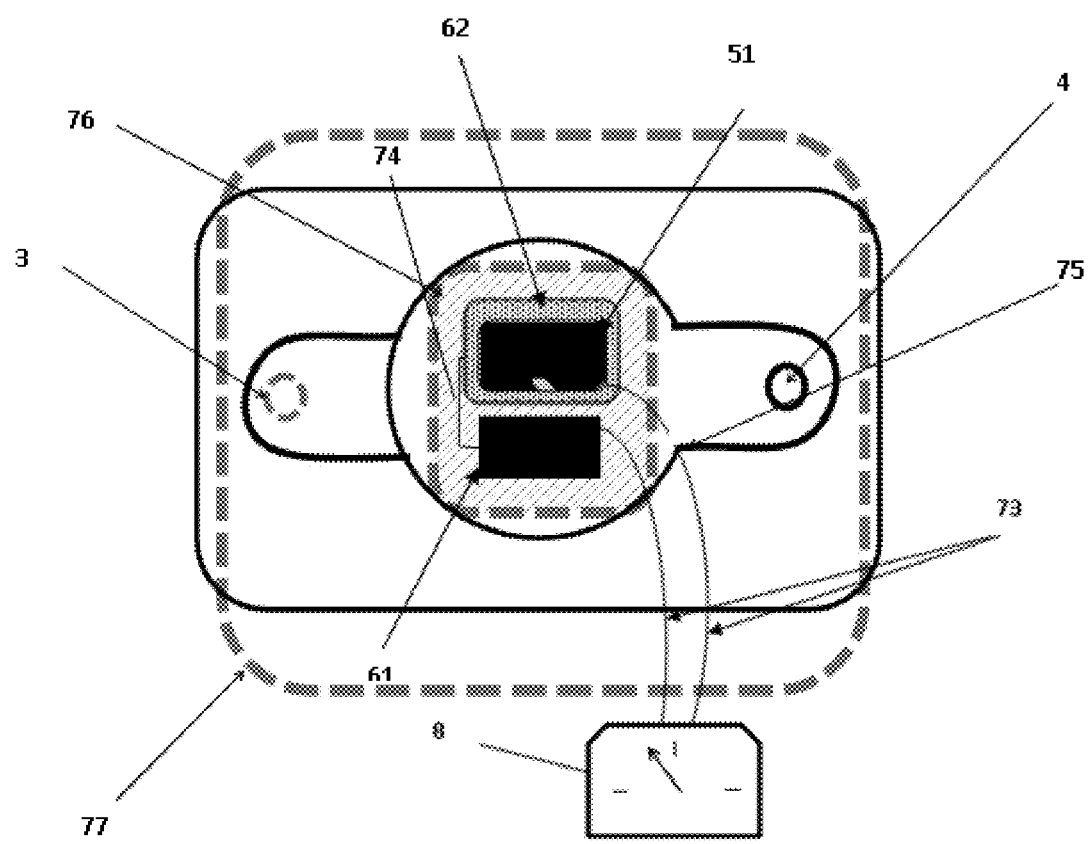
Figure 10:
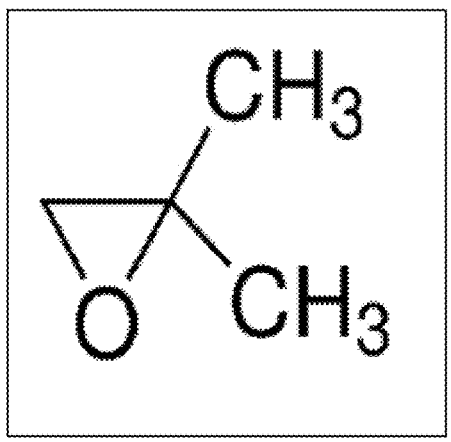
FIG. 10 shows a schematic view of 1,2-epoxy-2-methylpropane.
Figure 11:
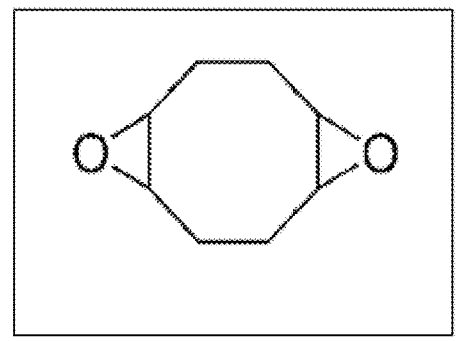
FIG. 11 shows a schematic view of 1,2,5,6-diepoxycyclooctane.
Figure 12:
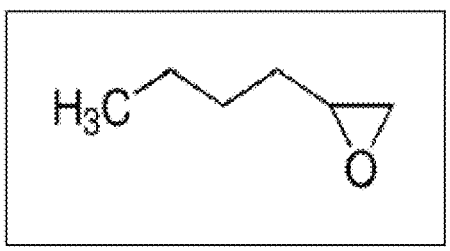
FIG. 12 shows a schematic view of 1,2-epoxyhexane.
Figure 13:
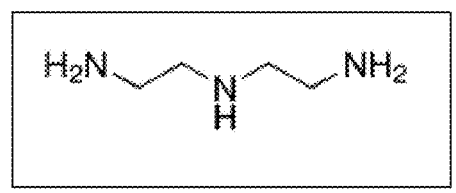
FIG. 13 shows a schematic view of Diethylenetriamine.
Figure 14:
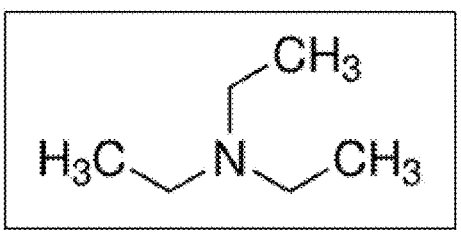
FIG. 14 shows a schematic view of Triethyl amine.
Figure 15:
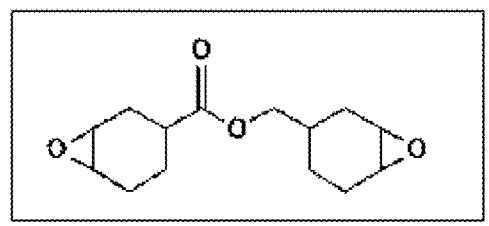
FIG. 15 shows a schematic view of 3',-4'-(Epoxycyclohexane)methyl 3',-4'-Epoxycyclohexyl-carboxylate.
Figure 16:
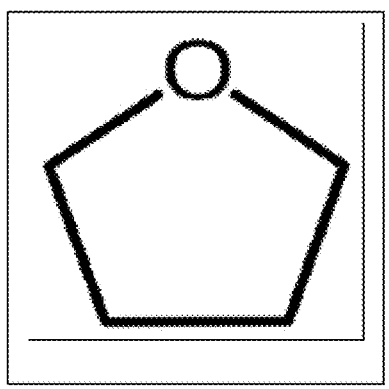
FIG. 16 shows a schematic view of Tetrahydrofuran.
Figure 17:
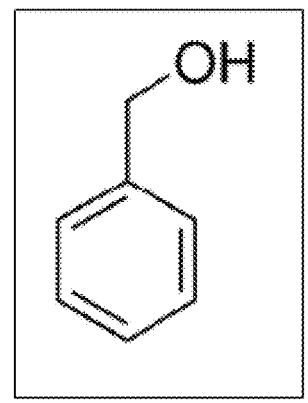
FIG. 17 shows a schematic view of Benzylic Alcohol.
Figure 18:
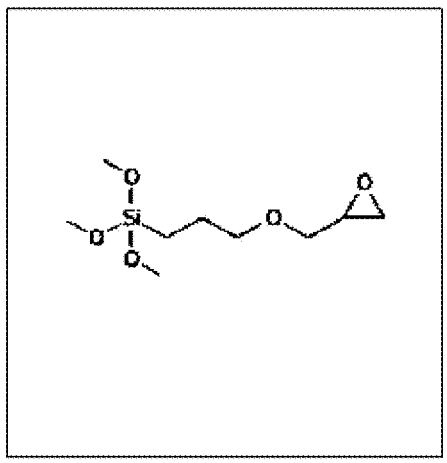
FIG. 18 shows a schematic view of (3-Glycidoxypropyl) Trimethoxysilane (Silquest A187)
Figure 19:
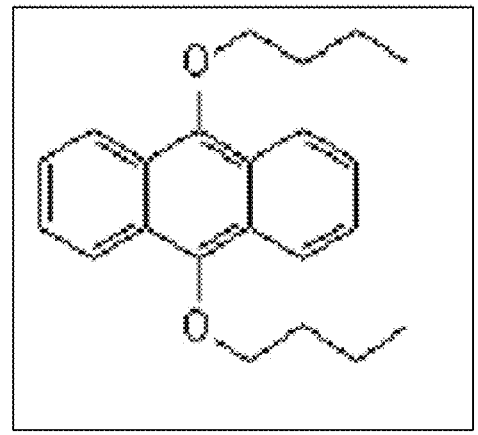
FIG. 19 shows a schematic view of 9,10-Dibutoxyanthracene (Anthracure UVS1331)
Figure 20:
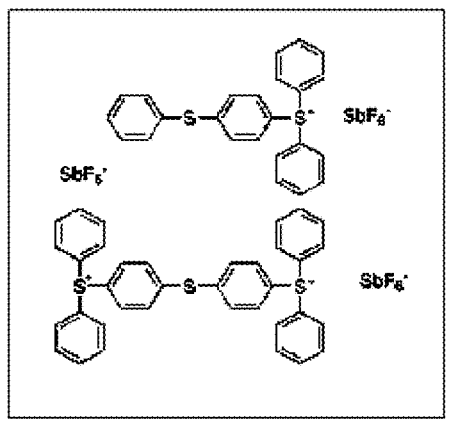
FIG. 20 shows a schematic view of Triarylsulfonium hexafluoroantimonate salt (1:1 in propylene carbonate)
Figure 21:
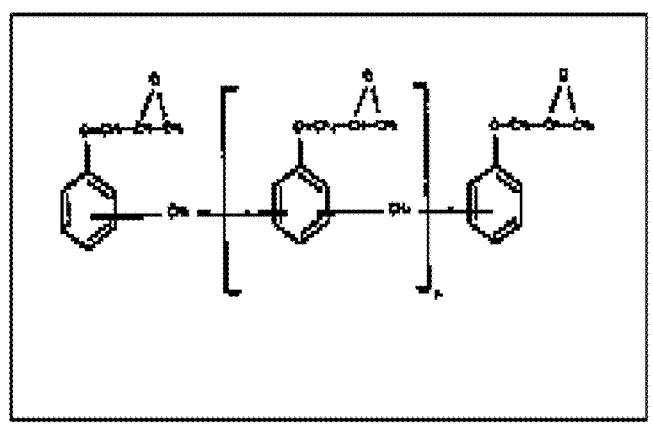
FIG. 21 shows a schematic view of Araldite ECN9699.
Figure 22:
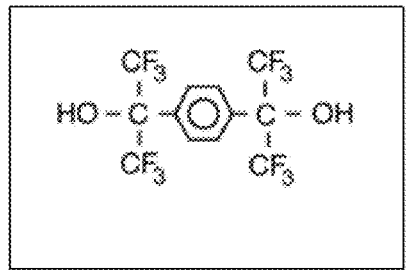
FIG. 22 shows a schematic view of 1,4-Bis(hexafluoro-2-hydroxy-2-propyl)benzene [1,4-HFAB].

FIGS. 7, 8, and 9 show schematic views of a dual sensor differential enthalpy vapor detecting device (bottom layer) according to an embodiment of the present invention. Specifically, in conjunction with these figures it is described an alternative device configuration with a higher sensitivity able to generate and detect vapors and more in general volatile fractions from the marked fuel or liquid. This configuration and the related methodology concentrate the marker contained into the fuel increasing the final output signal. This device comprises a heater element 76 (e.g. an electrical resistor) on the bottom layer (cf. FIG. 7); this bottom layer 77 could be a simple PCB which contains an inlet hole 3. On the top layer (cf. FIG. 8) there is arranged a microhydraulic circuit 75 which is preferably bonded to the bottom of the device; this channel can thus convey the liquid on the heater element 76 where it is heated to a specific temperature next to the boiling point of the marker, with preferably a controlled rate. The vapor having a concentrated fraction of marker can thus contact the two sensors 62 and 61, and the reactive polymer 51 nearby sensor 62 can react with the concentrated marker giving a characteristic signal function of the reaction enthalpy between vaporized marker and reactive polymer. The fuel or liquid could contain more than one marker with different boiling points. In general, different markers can be detected separately as the temperature increases. Preferably, the device is adapted to work at atmospheric pressures thanks to the outlet hole 4.

The configuration described in FIG. 9 provides a signal having less background noise (due to contact between polymer and not-reactive fuel fraction) and which is, in an advantageous manner, in principle able to detect very low concentrations of the one or more markers. Finally, this method may also increase the selectivity by introducing a crossing evaluation of physical properties of each molecule marker (the boiling point) in parallel to the enthalpy reaction with a reactive polymer.

Different chemical species diluted into the diesel fuel (provided by ENI) at a concentrations of 100 ppm have been tested as markers: 1,2-epoxy-2-methylpropane; 1,2,5,6-diepoxycyclooctane; 1,2-epoxyhexane; and diethylenetriamine. These markers are listed below in Table 1, and their molecular structures are reported in FIGS. 10 to 15. The output voltage levels detected with the pyroelectric device were in the range 1 to 5 mV, depending on the additive type.

The epoxy compounds are able to react with the chemical species released by the photopolymer, e.g. on the surface of the photopolymer by well-known cationic polyaddition ring opening reaction initiated by an acid released from the photopolymer. The amine tested is able to react with the released chemical species, i.e. an acid in this case, on or close to the surface of the photopolymer by a common acid-base reaction.

The different reaction mechanisms are well noticeable by evaluating the kinetics of the reaction: the epoxy ring opening reactions are faster than the amine reaction. This demonstrates that even within the same molecular class it is possible to distinguish between the presence of a certain compound employed as a marker and another by monitoring the intensity of the signal with respect to the reaction time. For example, two solutions containing different epoxy molecules in the same concentration in weight, but having different epoxy equivalent values or different degrees of molecule mobility, will typically give a different voltage signal.

Other possible reactive compounds commercially available from supplies such as Sigma Aldrich and which are considered suitable for the use as marker in the present invention are listed in Table 3.

The photopolymer forms a reactive coating in the device. The components used in the formulation are summarized in Table 4. Their molecular structures are reported in FIGS. 16 to 22.

Three formulations, used for the application, are listed in Table 5 for comparison. All of them were adopted, but the preferred one is F241W.

The reactivity toward markers in table 2 have been tested by means of DSC instrument by introducing each pure marker in contact to the photopolymer. The instrument records the heating or cooling signal characteristic of the reaction.

Each molecule tested in table 1 provides an appreciable heating or cooling signal detectable by DSC instrument. The pyroelectric sensor is able to detect exothermic and endothermic reactions between marker and photopolymer. In table 2 some reactive markers toward polymeric formulation F241W have been tested by means of DSC equipment. Pure diesel has been tested as well showing no appreciable DSC signal.

DSC evaluations have been executed with the following procedure:
Deposition of a known quantity of photopolymerizable composition into an aluminum pot;
UV exposure of the photopolymerizable composition by means of UV Fusion equipment with exposure energies equals or higher than 2000 mJ/cm2 in UVA, UVB, UVC region;
Deposition of the UV exposed sample into DSC instrument;
Deposition of a small amount of one marker listed in table 2 in contact with the UV exposed photopolymer;
Detecting of the characteristic heat of reaction.

In table 2 are also listed solubility data of tested markers in diesel fuel.

All the formulations are in form of liquid and could be dispensed on the desired surface by spray or spin or dip coating techniques or also using a microsyringe. Once dispensed, the polymeric composition could be photocured using a UV radiation source with an emission wavelength in the range of 250 to 450 nm. In this specific case, the irradiation causes the decomposition of the photoinitiator and further leads to the generation of super acid species that are stabilized in the photopolymer matrix. After the reticulation, the photopolymer is ready to use, without any additional process.

As previously mentioned, the photopolymeriazble composition can be dispensed either on the internal walls of the reaction chamber or onto the surface of the pyroelectric sensor; the latter solution could provide a better heat transfer to the sensor, if the polymer coating layer is very thin.

Three photocurable epoxy compositions exhibiting an excess of photoinitiators have been used to prepare the photopolymer in the reaction chamber of the detection device. These photopolymers are able to release acidic species upon contact with a liquid, such as fuel. Their compositions before UV irradiation are listed in table 5. The components are listed in table 4.

TABLE 1

Additives tested in the fuel

| Additive name | By |
|---|---|
| 1,2-epoxy-2-methylpropane | |
| 1,2,5,6-diepoxycyclooctane | Sigma-Aldrich |
| 3',4'-(Epoxycyclohexane)methyl3',4'- Epoxycyclohexyl-carboxylate | |
| 1,2-epoxyhexane | |
| Diethylenetriamine | |
| Triethylamine | |

TABLE 2

List of marker tested on F241W polymer formulation

| Ingredients | Maximum evaluated concentration of marker soluble into diesel fuel | Heat Variation |
|---|---|---|
| 1,2-epoxy-2-methylpropane (Sigma-Aldrich) | ≤10000 ppm | Exothermic |
| 1,2,5,6-diepoxycyclooctane (Sigma-Aldrich) | ≤100 ppm | Exothermic |
| 3',4'-(Epoxycyclohexane) methyl 3',4'-Epoxycyclohexyl- carboxylate (Sigma-Aldrich) | ≤10000 ppm | Exothermic |
| 1,2-epoxyhexane (Sigma-Aldrich) | ≤1000 ppm | Exothermic |
| Diethylenetriamine (Sigma-Aldrich) | <100 ppm | Exothermic |
| Triethylamine (Sigma-Aldrich) | ≤1000 ppm | Endothermic |
| Diesel fuel (ENI) | / | No signal |

TABLE 3

List of possible epoxy additives

| Name | Molecular Formula |
|---|---|
| Allyl glycidyl ether | $C_6H_{10}O_2$ |
| Bis[4-(glycidyloxy)phenyl]methane | $C_{19}H_{20}O_4$ |
| 1,3-butadiene diepoxide | $C_4H_6O_2$ |
| 1,4-butanediol diglycidyl ether | $C_{10}H_{18}O_4$ |
| Butyl glycidyl ether | $C_7H_{14}O_2$ |
| tert-butyl glycidyl ether | $C_7H_{14}O_2$ |
| 1,4-cyclohexanedimethanol diglycidyl ether | $C_{14}H_{24}O_4$ |
| Cyclohexene oxide | $C_6H_{10}O$ |
| Cyclopentene oxide | $C_5H_8O$ |
| Dicyclopentadiene dioxide | $C_{10}H_{12}O_2$ |
| Dieldrin | $C_{12}H_8Cl_6O$ |

TABLE 3-continued

List of possible epoxy additives

| Name | Molecular Formula |
|---|---|
| 1,2,7,8-diepoxyoctane | $C_8H_{14}O_2$ |
| Diglycidyl 1,2-cyclohexanedicarboxylate | $C_{14}H_{20}O_6$ |
| N,N-diglycidyl-4-glycidyloxyaniline | $C_{15}H_{19}NO_4$ |
| 1,2-epoxybutane | $C_4H_8O$ |
| 2,3-epoxybutane | $C_4H_8O$ |
| 3,4-epoxy-1-butene | $C_4H_6O$ |
| 3,4-epoxycyclohexylmethyl-3,4-epoxycyclohexanecarboxylate | $C_{14}H_{20}O_4$ |
| 1,2-epoxydodecane | $C_{12}H_{24}O$ |

TABLE 4 list of the polymer components

ARALDITE ® ECN9699
Huntsmann's aromatic epoxy oligomer derived from Novolac resin
1,4-HFAB
Fluorinated aromatic diol by Central Glass, used in a cationic system as a chain transfer promoter
1331-UVS ANTHRACURE ®
Photosensitizer for cationic systems produced by Kawasaki Kasei Chemicals LTD.
Triarylsulfonium hexalfuoroantimonate salt
(1:1 in propylene carbonate)
Cationic photoinitiator useful to generate the superacid by means of UV irradiation, from Sigma-Aldrich.
(3-Glycidoxypropyl) Trimethoxysilane (SILQUEST ® A187)
Adhesion promoter by MOMENTIVE ®.
Byk 310
Non ionic silicone-containing surface additive for solvent-free and solvent-borne coating systems, by Byk Chemie
Tetrahydrofuran and Benzylic alcohol
Common organic solvents by Sigma-Aldrich ARALDITE® ECN9699 is an aromatic epoxy oligomer used into the formulation; it defines, after the polymerization step, the chemical, physical and mechanical properties of the polymer. This oligomer is able to reticulate by cationic polyaddition mechanism.

1,4-HFAB is a diol used into the formulation as a chain transfer agent for the cationic polyaddition of the epoxy monomer/oligomer (ARALDITE® ECN9699). This component contributes to an increase of epoxy conversion into the final polymer. It also reduces the reticulation density of the polymer, increasing its flexibility.

1331-UVS ANTHRACURE® is an anthracene compound used in order to absorbe UV-Vis radiation at wavelengths where the photoinitiator is not photosensible. The 1331-UVS ANTHRACURE® excited state induces decomposition of the photoinitiator and consequent generation of superacid polymerization initiator.

Triarylsulfonium hexalfuoroantimonate salt is a photoinitiator that initiates, under UV radiation exposure, the epoxy ring opening. UV irradiation at certain wavelengths produces photoinitiator decomposition and consequent superacid initiator generation (hexafluoroantimonic acid). Once the epoxy reticulation is concluded all the superacid excess remain absorbed into the polymeric structure.

(3-Glycidoxypropyl) Trimethoxysilane (SILQUEST® A187) is an adhesion promoter able to react contemporary with polar groups present on a surface (typically hydroxides, amines and thiols) and the epoxy based formulation, developing high adhesion between the polymer and the surface.

Byk 310 is a surfactant useful for solvent based systems to reduce their surface tension. It increases the wettability of liquid formulation, before its reticulation, toward surfaces like plastic, metals, etc. . . . .

Tetrahydrofuran and Benzylic alcohol (phenol) are two common organic solvents useful to solubilize all the ingredients inside an homogeneus low viscous formulation. Organic solvents contribute to reduce surface tension of the liquid formulation.

TABLE 5

Further Embodiments

| Name | F239W . . . | F240W % Wt | F241W . . . |
|---|---|---|---|
| ARALDITE ® ECN9699 | 44.24 | 44.24 | 22.12 |
| Benzylic alcohol | 28 | 0 | 0 |
| Tetrahydrofuran | | 28 | 14 |
| 1,4-bis(hexafluoro-2-hydroxy-2-propyl)benzene [1,4-HFAB] | 10 | 10 | 5 |
| (3-glycidoxypropyl) trimethoxysilane [SILQUEST ® A187] | 5.14 | 5.14 | 2.57 |
| 9,10-dibuthoxyanthracene [1331-UVS ANTHRACURE ®] | 0.47 | 0.47 | 0.23 |
| Triarylsulfonium hexalfuoroantimonate salt (1:1 in propylene carbonate) | 12 | 12 | 56 |
| Byk 310 | 0.15 | 0.15 | 0.075 |

The ingredients listed in table 4 and 5 are ARALDITE® ECN9699, Triarylsulfonium hexafluoroantimonate salt and one organic solvent in order to solubilize these two components.

In principle any photopolymerizable composition having epoxy based oligomers/monomers can be used in the present invention. The photoinitiator contained therein should be able to produce a suitable amount of acid (preferably superacid) after UV exposure. In many instances it is observed that the higher the pKa value of the acid, the higher is the heating or cooling signal is detected by the pyroelectric sensor.

So it is preferable to have photoinitiators having anions of superacids, like hexafluoroantimonate, hexafluorophosphate, Tris(4-(4-acetylphenyl)thiophenyl)sulfonium tetrakis(penta-fluorophenyl)borate, or tris(trisfluoromethanesulfonyl)methide.

If an epoxy-based photopolymer capable of releasing an acid is used, and the acid released therefrom is derived from a decomposed photoinitiator, a correct value of the starting ratio epoxy/photoinitiator is important. A photoinitiator weight ratio equal to higher than 10%, preferably equal to or higher than 50%, and in some cases equal to or higher than 100% with respect to the epoxy starting material prior to the formation of the photopolymer (i.e. before irradiation) is preferable.

After UV irradiation, some of the initiator will be consumed, and possibly there is also a certain loss of more volatile fractions. The formed photopolymer after UV irradiation preferably contains acids and/or unreacted photoinitiator in an amount of 0.1-5% by weight, or 1-8% by weight, or 2-10% by weight, in order to have a good reactivity with the marker.

It is self-evident to the skilled person that the organic solvents used in the formulation should not inhibit the photogeneration of e.g. acid species or the stabilization of carbocationic species in the epoxy fraction. It is therefore preferable to exclude the presence of any basic compound in the formulation, such as amines, amides, azotate cycles, thiols, sulfides.

Suitable solvents like alcohols, ethers, esters, aromatic hydrocarbons, glycoethers could be useful to dilute the formulation.

It is preferable to have a polymer like F241W having an intrinsic ability to be swelled by the marker contained into the fuel; the higher the marker permeation is, the higher is the reaction volume and consequently the higher is the signal detected by the pyroelectric sensor.

It is preferable to use a polymer which is soft, i.e. exhibits a low glass transition temperature (Tg) of 150° C. or less, preferably 130° C. or less. In such a way, the release of acid from the polymer is facilitated. At a temperature change rate of 10° C./min between 25 and 200° C. we have measured the following values of Tg for the polymers obtained by the photocurable compositions in Table 5:

F239W and F240W: Tg=124° C.
F241W: Tg=54° C.

The used photopolymer exhibits therefore preferably a Tg between 25° and 150° C., more preferably between 45° and 130° C.

The markers proposed in this invention are difficult to be found out once dissolved into the fuel, and their detection is performed using a specific (and typically unknown) polymer. Therefore, the present invention provides a method for authenticating a material marked with a marker, as a person wishing to forge the liquid would not only have to find out about the presence and concentration of the marker, but would also need to know which kind of polymer is used in the device.

Although detailed embodiments have been described, these only serve to provide a better understanding of the invention defined by the independent claims, and are not to be seen as limiting.

The invention claimed is:

1. A detection device for detecting a marker in a liquid, comprising:
   a reaction chamber;
   a thermosensitive sensor placed in the reaction chamber; and
   a photopolymer layer capable of releasing or generating a chemical species that is capable of undergoing or initiating an exothermic or endothermic chemical reaction with a marker present in the liquid, wherein the photopolymer layer is deposited on the walls and/or on the floor of the reaction chamber and/or on the thermosensitive sensor,
wherein the photopolymer layer is obtainable by a method comprising the following steps:
   a step of depositing a layer of a photocurable epoxy composition exhibiting an excess of photoinitiator on the walls and/or on the floor of the reaction chamber and/or on the thermosensitive sensor itself;
   a step of photocuring with UV radiation the layer of the photocurable epoxy composition exhibiting an excess of photoinitiator, so that exceeding unreacted acid molecules are left adsorbed in the bulk and/or on the surface of an acidified photopolymer layer.

2. The detection device according to claim 1, further comprising any one of:
   a liquid-resistant substrate;
   an injection chamber in communication with the reaction chamber exhibiting an inlet for introducing the liquid; and
   an outlet, connected to the reaction chamber.

3. The detection device according to claim 1, further comprising:
   a heater element placed on a bottom layer of the detection device suitable to heat and to evaporate a marker dissolved in the liquid, and to convey the evaporated marker dissolved in the liquid towards the thermosensitive sensor, and wherein the thermosensitive sensor is coated with the photopolymer layer, and the exceeding unreacted acid molecules are capable to promote an exothermic or endothermic chemical reaction with the evaporated marker dissolved in the liquid.

4. The detection device according to claim 1, wherein the thermosensitive sensor is a pyroelectric sensor, and further comprises:
   at least two conductive tracks transmitting signals generated by the pyroelectric sensor to a current or voltage measurement device.

5. The detection device according to claim 1, wherein a marker diluted in the liquid at a concentration smaller than 150 ppm generates on a voltage measurement device a voltage greater than 1 mV.

6. The detection device according to claim 1, wherein the photocurable epoxy composition comprises:
   a) 20 to 50% wt of an epoxy monomer or oligomer;
   b) 5 to 60% wt of a cationic photoinitiator;
   c) 10 to 30% wt of an organic solvent;
   based on the total weight of the photocurable composition.

7. The detection device according to claim 1, wherein a ratio epoxy equivalents/acid equivalents of the photocurable composition used to produce the acidified photopolymer layer is between 18 and 1.

8. The detection device according to claim 1, wherein the liquid is a fuel and the marker is a diluted marker dissolved in said fuel.

9. A system comprising:
   A. a detection device according to claim 1;
   B. a fuel as said liquid;
   C. a marker dissolved in the fuel with a concentration <150 ppm, which is an epoxy compound.

10. A method for manufacturing a detection device according to claim 1 comprising the steps of:
   depositing a layer of a photocurable epoxy composition exhibiting an excess of photoinitiator on the walls and/or on the floor of a reaction chamber and/or on a thermosensitive sensor placed in the reaction chamber;
   photocuring with UV radiation the layer of the photocurable epoxy composition exhibiting an excess of photoinitiator, so that unreacted acid molecules resulting from the decomposition of the photoinitiator maintain in the bulk and/or on the surface of an acidified photopolymer layer.

11. The method according to claim 10, wherein the photocurable epoxy composition comprises:
   a) 20 to 50% wt of an epoxy monomer or oligomer;
   b) 5 to 60% wt of a cationic photoinitiator;
   c) 10 to 30% wt of an organic solvent;
   based on the total weight of the photocurable composition.

12. The method according to claim 10, wherein a ratio of epoxy equivalents/acid equivalents of the photocurable composition used to produce the acidified photopolymer layer is between 18 and 1.

13. A method for detecting a marker in a liquid, comprising the steps of:
   introducing a marked liquid into the reaction chamber of a detecting device according to claim 1;
   letting the marker react in the reaction chamber with the exceeding unreacted acid molecules released or generated from the photopolymer layer to cause a temperature increase or decrease at the position of the thermosensitive sensor by an exothermic or endothermic reaction of the marker and the exceeding unreacted acid molecules released or generated from the photopolymer layer; and measuring a voltage or current output generated by the thermosensitive sensor placed in the reaction chamber.

14. The method according to claim 13, wherein the liquid is a fuel and the marker is a diluted marker dissolved in said fuel.

15. The method according to claim 13, wherein the liquid contains more than one marker, the exceeding unreacted acid molecules released or generated by the photopolymer layer are able to cause a reaction with the more than one of the markers, and an obtained voltage and current output generated by the thermosensitive sensor is representative for the presence and/or concentration of the more than one marker.

16. The method according to claim 13, wherein the marker is a compound that reacts with the exceeding unreacted acid molecules by ring-opening or polymerization.

17. The detection device according to claim 1, wherein the exceeding unreacted acid molecules are superacid molecules.

18. The detection device according to claim 4, wherein the current or voltage measurement device is an oscilloscope.

19. The method according to claim 15, wherein the liquid contains two or three markers.

20. The method according to claim 16, wherein the exceeding unreacted acid molecules are is superacid molecules.

21. The method according to claim 16, wherein the marker is a compound having one or more epoxy groups or a compound having one or more ethylenically unsaturated groups.

* * * * *